United States Patent [19]

Ambler

[11] 4,292,154

[45] Sep. 29, 1981

[54] BUFFER COMPOSITION AND METHOD FOR THE ELECTROPHORETIC SEPARATION OF PROTEINS

[75] Inventor: Jeffrey Ambler, Tollerton, England

[73] Assignee: Gelman Sciences, Inc., Ann Arbor, Mich.

[21] Appl. No.: 138,384

[22] Filed: Apr. 8, 1980

Related U.S. Application Data

[63] Continuation-in-part of Ser. No. 92,250, Nov. 7, 1979, abandoned.

[51] Int. Cl.$^3$ .................... G01N 33/16; G01N 27/26
[52] U.S. Cl. ........................ 204/180 G; 204/180 S; 204/299 R; 23/912
[58] Field of Search ............... 204/180 G, 180 S, 299; 23/230 B, 902, 912; 252/184; 424/308, 309, 310

[56] References Cited

U.S. PATENT DOCUMENTS 4,243,749  1/1981  Sadeh et al. .................. 23/230 B X
4,246,084  1/1981  Gurske ........................... 204/180 G

*Primary Examiner*—Arthur C. Prescott
*Attorney, Agent, or Firm*—Reising, Ethington, Barnard, Perry & Brooks

[57] ABSTRACT

A buffer composition for use in the electrophoretic separation of proteins into fractions, the buffer composition consisting essentially of Tris; an acid having the formula $R_1$—CO—NH—$R_2$—COOH where $R_1$ is $NH_2$ or an alkyl or aryl group, preferably $NH_2$, $C_6H_5$ or $C_6H_4NH_2$ and where $R_2$ is an alkyl group, preferably $CH_2$, $CH_2$—$CH_2$ or $CH(CH_3)$; and a water soluble salt of the acid; the acid and salt being present in amounts and in a ratio to maintain the pH of an aqueous solution of the composition at from 8.2 to 9.0. The preferred acid is hippuric acid.

11 Claims, No Drawings

BUFFER COMPOSITION AND METHOD FOR THE ELECTROPHORETIC SEPARATION OF PROTEINS

This application is a continuation-in-part of application Ser. No. 92,250 filed Nov. 7, 1979 entitled "Buffer Composition and Method for the Electrophoretic Separation of Proteins", the entire disclosure of which is incorporated herein by reference, said application now abandoned.

TECHNICAL FIELD

The subject matter of the present invention is a buffer composition and method for the electrophoretic separation of proteins into fractions. The buffer composition and method of the present invention find particular utility as replacements for electrophoretic procedures and buffers which are currently used for the separation of proteins and which involve the use of barbiturates.

BACKGROUND ART

It is well known that a protein material can be separated into different fractions of different densities or mobilities by electrophoresis. In the practice of this technique the protein sample to be fractionated is placed on the surface of a substrate which is immersed in, or otherwise saturated with, a so-called buffer solution, whereupon an electrical current is applied sufficient to cause migration, by way of electrophoresis, of the protein material into fractions of different mobilities, the fractions being spaced from each other, on the substrate, between the anode and cathode. After the separation is complete, it then only becomes a matter of determining the relative quantities of the fractions by any of various techniques equally well known in the art.

The buffer solution currently in common use for such protein analyses includes a barbiturate as its key ingredient. That is, the buffering function is provided by a combination of barbituric acid and a salt of barbituric acid. The main disadvantage to this has been, and continues to be, that the barbiturates are "controlled substances" under the drug control laws and regulations of the United States, and under similar laws and regulations of other countries. Hence, in the manufacture, distribution, sale and use of such buffers, accountability and administrative control are required, with much attendant trouble and expense. It is particularly for this reason that there has been a long felt need for a non-barbiturate buffer composition which is as effective as the currently used barbiturate buffers for the electrophoretic separation of protein materials.

The present invention fulfills this need.

DISCLOSURE OF INVENTION

Restating here what is stated in my earlier aforesaid U.S. patent application, of which this is a continuation-in-part, what I first discovered was that Tris [2-amino-2-(hydroxymethyl)-1,3-propanediol] in combination with hippuric acid and a water soluble hippurate provides a buffer solution which, though it doesn't involve the use of barbiturate or any other controlled substance, is as effective as, and in some respects superior to, the barbiturate buffers heretofore used in the electrophoretic separation of proteins. What I have now further discovered is that analogues of hippuric acid, and its salt, having the structural formula hereinafter set forth can be substituted for the hippuric acid and its salt with advantages which, though not as great as with respect to the preferred hippuric acid-hippurate, are nevertheless comparable and provide the wherewithal of attaining a good electrophoretic separation of proteins without the use of barbiturates. But before proceeding to describe the analogues I will here first go on to repeat the disclosure of the aforesaid earlier patent application with respect to hippuric acid-hippurate.

The Tris should preferably be present in the solution in an amount of from about 5 to 8 grams per liter, and the amounts and ratio of the amounts of hippuric acid and the water soluble hippurate should be such as to provide the solution with a pH of from 8.2 to 9.0. The alkali metal hippurates are preferred because of their relatively high solubility in water, the preferred concentration for the sum of the hippurate and hippuric acid being from about 5 to 15 grams per liter, which is from about 0.03 to 0.08 moles per liter. Particularly good results have been obtained using from about 6 to 10 grams per liter hippurate and from about one-fourth to one-half that amount of hippuric acid, the precise ratio and the precise concentration of the Tris being such as to provide the desired pH of from 8.2 to 9.0.

I theorize and test results appear to verify, that the hippuric acid and hippurate function not only to buffer the solution to the desired pH but also as complexing agents, bonding—probably by hydrogen bonding—to the proteins thereby altering their mobilities during the electrophoresis. Additionally, the hippurate in particular, and also the hippuric acid to some extent, provide an increase in the ionic strength of the solution thereby increasing its current carrying capacity. The Tris provides some buffering and is theorized to also function, at least to some extent, in increasing the current carrying capacity of the solution. If, as will often be the case, it is desired to further increase the ionic strength, and hence the current carrying capacity of the solution, this can be accomplished by the addition of a water soluble inorganic salt, preferably an alkali metal halide such as sodium chloride, and preferably in an amount of from 0.5 to 3 grams per liter.

For the practice of the invention it is generally preferred as a matter of convenience, to prepare a mixture of the Tris, hippuric acid and hippurate (and inorganic salt if such is desired to be included) in solid, dry form with the ratio of these ingredients being such that when sufficient of the mixture is dissolved in water to provide the preferred Tris concentration of from 5 to 8 grams per liter, the amount of hippuric acid and hippurate present in the solution will be such as to provide a pH from 8.2 to 9.0.

As has been indicated above, the buffer compositions of the present invention are intended to replace the currently used barbiturate buffering compositions, and they can be used in all electrophoretic procedures and with all substrates where barbiturate buffering solutions are or have been used. Hence, the substrate used can, for example, be agarose gel or membrane such as cellulose acetate membrane; and the electrophoretic procedure can be either one of zone electrophoresis or one of immunoelectrophoresis. For example, using agarose, the buffer may be used for electrophoresis systems which identify lipoproteins, proteins or isoenzymes. The buffer may also be used to support systems in which immunoelectrophoresis techniques are carried out, either by fixation, diffusion, or electrodiffusion. Such techniques, for example, as the Rocket technique of Laurel, may be carried out with equal success on agarose or cellulose acetate membrane.

The structural formula for the preferred hippuric acid is $C_6H_5-CO-NH-CH_2-COOH$ and I have now found that for the effective electrophoretic separation of proteins into its fractions there can be substituted therefor its water soluble analogues having the structural formula $R_1-CO-NH-R_2-COOH$ where $R_1$ is $NH_2$ or an alkyl or aryl group, preferably either $NH_2$, $C_6H_5$ or $C_6H_4NH_2$ and where $R_2$ is an alkyl group, preferably $CH_2$, $CH(CH_3)$ or $CH_2-CH_2$. Included in this group of analogues are:

N-benzoyl-α-alanine $C_6H_5-CO-NH-CH(CH_3)-COOH$

N-benzoyl-β-alanine $C_6H_5-CO-NH-CH_2-CH_2-COOH$ hydantoic acid (carbamoyl glycine)

$NH_2-CO-NH-CH_2-COOH$ p-aminohippuric acid $NH_2-C_6H_4-CO-NH-CH_2-COOH$

The combination of the acid and its water soluble salt, preferably the sodium salt, can be used in place of the hippuric acid and its salt in the buffer composition, in the same molar concentrations and ratios and with the other ingredients and conditions being the same as stated above with respect to hippuric acid and hippurate. That is, the Tris should preferably be present in an amount within the range of from about 5 to 8 grams per liter, and the combination of the water soluble salt and the acid should preferably be present in an amount of from 0.03 to 0.08 moles per liter, the ratio of salt to acid, and the precise concentration of the Tris from within the above range being such as to provide a pH of from 8.2 to 9.0. Just as in the case where hippuric acid and hippurate are used, so also with these analogues the current carrying capacity of the solution can be accomplished by the addition of a water soluble inorganic salt, preferably sodium chloride and preferably in an amount of from 0.5 to 3 grams per liter. Likewise, the use and range of use of these analogue based buffers in the electrophoretic separation of proteins is as taught above with respect to the preferred hippuric acid-hippurate buffer.

BEST MODE FOR CARRYING OUT THE INVENTION

The most preferred composition of the present invention contains the following as its essential ingredients, in amounts to provide, when dissolved in water, the amount per liter indicated for each ingredient:

EXAMPLE 1

| Tris | 6.0 g/l |
|---|---|
| Hippuric Acid | 2.5 g/l (.014 moles/l) |
| Sodium Hippurate | 8.0 g/l (.040 moles/l) |
| pH | 8.8 |

The following is a typical electrophoretic method wherein the immediately aforesaid composition is used for the buffer solution:

A cellulose acetate membrane is equilibrated with the buffer solution for at least 10 minutes prior to use whereby it is saturated with the solution. After removing excess moisture from the surface, the membrane is placed in a conventional electrophoresis chamber, making contact at either end with the buffer solution present in the two electrode compartments of the chamber. The sample is applied and electrophoresis carried out at a suitable voltage (typically 175–225 volts) and for a suitable time (typically 20–30 minutes) thereby to cause the separation of the protein sample into fractions. The sample separation is then stained with a protein stain such as Ponceau S, the membrane is cleared and the protein fractions quantitated using a densitometer. Five protein fractions are obtained in the same manner as with barbiturate buffer, so that reliable quantitation may be carried out. In addition to the fact that the buffer is composed of non-dangerous components, it has advantage over barbiturate in other regards, particularly in that it is less expensive and is more stable at room temperature.

Examples of other buffer solutions which embody the invention and can be used in place of the aforesaid Example are as follows:

EXAMPLE 2

| Tris | 6.9 g/l (.057 moles/l) |
|---|---|
| N-benzoyl-DL-alanine | 2.3 g/l (.012 moles/l) |
| sodium N-benzoyl-DL-alanine | 7.7 g/l (.036 moles/l) |
| pH | 8.8 |

EXAMPLE 3

| Tris | 6.0 g/l (.05 moles/l) |
|---|---|
| N-benzoyl-β-alanine | .6 g/l (.003 moles/l) |
| sodium N-benzoyl-β-alanine | 11.0 g/l (.051 moles/l) |
| pH | 8.8 |

EXAMPLE 4

| Tris | 6.0 g/l (.05 moles/l) |
|---|---|
| Hydantoic acid | .7 g/l (.006 moles/l) |
| Sodium hydantoate | 6.7 g/l (.048 moles/l) |
| pH | 8.8 |

In making up the buffer solution, irrespective of whether the preferred hippuric acid or one of the analogues is used, the acid and its salt can be added as such or alternatively, just the acid can be added as such and then the solution titrated to the desired pH by the addition of hydroxide, e.g. sodium hydroxide to convert a portion of the acid to its salt, or by the addition of the Tris, or a portion of it, in an amount to accomplish the precise desired pH. For the convenience of the laboratory technician in preparing the solution it is generally preferred, however, that the buffer composition be prepared in dry form using the acid and its salt as such, to the end that it is only necessary to dissolve the composition in water in an amount to provide the concentration desired, the dry ingredients being present in a ratio, as aforesaid, to provide the desired pH.

Just as the barbiturate buffers used for the electrophoresis of proteins are also used for the immunodiffusion of proteins, so also the buffer compositions of the present invention are useful not only for electrophoresis but also for the immunodiffusion of proteins.

It will be understood that while the invention has been described in its particulars with reference to preferred embodiments, various changes and modifications may be made all within the full and intended scope of the claims which follow:

What is claimed is:

1. A method for electrophoretically separating proteins, said method comprising placing a sample of the proteins to be separated on a substrate, placing the substrate with said sample thereon in an electrically conductive buffer solution, and then passing an electric current through said solution thereby to cause the protein sample to separate, on said substrate, into fractions of different densities or mobilities, said buffer solution having a pH of from 8.2 to 9.0 and containing an acid having the formula $R_1-CO-NH-R_2-COOH$ where $R_1$ is $NH_2$, an alkyl group or an aryl group and where $R_2$ is an alkyl group, and a water soluble salt of the acid.

2. A method as set forth in claim 1 wherein, in said acid, $R_1$ is $NH_2$, $C_6H_5$ or $C_6H_4NH_2$ and $R_2$ is $CH_2$, $CH_2-CH_2$ or $CH(CH_3)$.

3. A method as set forth in claim 1 wherein concentration of the sum of the acid and salt in said solution is from about 0.03 to 0.08 moles per liter.

4. A method as set forth in claim 3 wherein said solution contains 2-amino-2-(hydroxymethyl)-1,3-propanediol in an amount of from about 5 to 8 grams per liter.

5. A method as set forth in claim 4 wherein said solution additionally contains a water soluble inorganic salt.

6. A method as set forth in claim 1, 3, 4 or 5 wherein the acid in said solution is N-benzoyl-α-alanine.

7. A method as set forth in claim 1, 3, 4 or 5 wherein the acid in said solution is N-benzoyl-β-alanine.

8. A method as set forth in claim 1, 3, 4 or 5 wherein the acid in said solution is hydantoic acid.

9. A method as set forth in claim 1, 3, 4 or 5 wherein the acid in said solution is p-aminohippuric acid.

10. A method as set forth in claim 1, 3, 4 or 5 wherein the acid in said solution is hippuric acid.

11. A method as set forth in claim 10 wherein said solution contains the 2-amino-2-(hydroxymethyl)-1,3-propanediol in an amount of about 6 grams per liter, the hippuric acid in an amount of about 2.5 grams per liter and the salt in an amount of about 8 grams per liter.

* * * * *